(12) United States Patent
Bray

(10) Patent No.: US 8,262,705 B2
(45) Date of Patent: Sep. 11, 2012

(54) SLIDABLE BONE PLATE SYSTEM

(75) Inventor: Robert S. Bray, Studio City, CA (US)

(73) Assignee: NuVasive, Inc., San Diego, CA (US)

( * ) Notice: Subject to any disclaimer, the term of this patent is extended or adjusted under 35 U.S.C. 154(b) by 1275 days.

(21) Appl. No.: 11/231,493

(22) Filed: Sep. 20, 2005

(65) Prior Publication Data
US 2006/0064097 A1 Mar. 23, 2006

Related U.S. Application Data

(62) Division of application No. 10/427,592, filed on May 1, 2003, now Pat. No. 6,945,973.

(51) Int. Cl.
*A61B 17/80* (2006.01)
(52) U.S. Cl. ............................ 606/280; 606/71; 606/295
(58) Field of Classification Search .......... 606/280–299, 606/70, 71
See application file for complete search history.

(56) References Cited

U.S. PATENT DOCUMENTS

| 6,945,973 B2 | 9/2005 | Bray |
| 2001/0047172 A1 | 11/2001 | Foley et al. |
| 2002/0065517 A1* | 5/2002 | Paul .............................. 606/69 |
| 2004/0087951 A1 | 5/2004 | Khalili |

FOREIGN PATENT DOCUMENTS

| WO | 9851226 A | 5/1998 |
| WO | 0222030 A | 3/2002 |
| WO | 02080789 A | 10/2002 |

* cited by examiner

*Primary Examiner* — Eduardo C Robert
*Assistant Examiner* — Christina Negrelli
(74) *Attorney, Agent, or Firm* — NuVasive, Inc.; Jonathan Spangler; Jennifer Russell

(57) ABSTRACT

The invention is directed to a bone plate system. The bone plate system comprises a base plate having two generally parallel elongated screw slots extending therethrough. Two bone screws are provided that are capable of securing the base plate to a bone by insertion through the screw slots into the bone. Each bone screw has a screw head and a threaded portion extending therefrom. An interference device is attached to the base plate and retains the bone screws while permitting the bone screws to toggle and to controllably slide in the screw slots of the base plate. This design is particularly useful for joining adjacent vertebral bodies, as it permits controlled settling of the vertebral bodies, thereby enhancing the healing process.

7 Claims, 5 Drawing Sheets

SLIDABLE BONE PLATE SYSTEM

CROSS REFERENCES TO RELATED APPLICATIONS

The present application is a divisional application of commonly owned and U.S. patent application Ser. No. 10/427,592, filed on May 1, 2003, now U.S. Pat. No. 6,945,973 the entire contents of which are hereby expressly incorporated by reference into this disclosure as if set forth fully herein.

BACKGROUND OF THE INVENTION

The spinal column of vertebrates provides support to bear weight and protection to the delicate spinal cords and spinal nerves. The spinal column comprises a series of vertebrae stacked on top of each other. There are typically seven cervical (neck), twelve thoracic (chest), and five lumbar (low back) segments. Each vertebra has a cylindrical-shaped vertebral body in the anterior portion of the spine with an arch of bone to the posterior that covers the neural structures. Between each vertebral body is an intervertebral disk, a cartilaginous cushion to help absorb impact and dampen compressive forces on the spine. To the posterior, the laminar arch covers the neural structures of the spinal core and nerves for protection. At the junction of the arch and anterior vertebral body are articulations to allow movement of the spine.

Various types of problems can affect the structure and function of the spinal column. These can be based on degenerative conditions of the intervertebral disk or the articulating joints, traumatic disruption of the disk, bone or ligaments supporting the spine, tumor or infection. In addition congenital or acquired deformities can cause abnormal angulation or slippage of the spine. Anterior slippage of one vertebral body on another (spondylolisthesis) can cause compression of the spinal cord or nerves. Patients who suffer from one or more of these conditions often experience extreme and debilitating pain, and can sustain permanent neurologic damage if the conditions are not treated appropriately.

One technique of treating these disorders is known as surgical arthrodesis of the spine. This can be accomplished by removing the intervertebral disk and replacing it with bone and immobilizing the spine to allow the eventual fusion or growth of the bone across the disk space to connect the adjoining vertebral bodies together. The stabilization of the vertebra to allow fusion is often assisted by a surgically implanted device to hold the vertebral bodies in proper alignment and allow the bone to heal, much like placing a cast on a fractured bone. Such techniques have been effectively used to treat the above described conditions and in most cases are effective at reducing the patient's pain and preventing neurologic loss of function. However, there are disadvantages to the present stabilization devices.

The spinal fixation device needs to allow partial sharing of the weight of the vertebral bodies across the bone graft site. Bone will not heal if it is stress shielded from all weight bearing. The fixation device needs to allow for this weight sharing along the micromotion that happens during weight sharing until the fusion is complete, often for a period of three to six month or longer, without breakage. The device must be strong enough to resist collapsing forces or abnormal angulation during the healing of the bone. Loss of alignment during the healing phase can cause a poor outcome for the patient. The device must be secure in its attachment to the spine to prevent migration of the implant or backout of the screws from the bone which could result in damage to the structures surrounding the spine, resulting in severe and potentially life threatening complications. The device must be safely and consistently implanted without damage to the patient.

SUMMARY OF THE INVENTION

The present invention is directed to a bone plate system that addresses one or more of the above drawbacks. In one embodiment, the bone plate system comprises a base plate having two generally parallel elongated screw slots extending therethrough. Two bone screws are provided that are capable of securing the base plate to a bone by insertion through the screw slots into the bone. Each bone screw has a screw head and a threaded portion extending therefrom. An interference device is attached to the base plate and retains the bone screws while permitting the bone screws to toggle and to controllably slide in the screw slots of the base plate. This design is particularly useful for joining adjacent vertebral bodies, as it permits controlled settling of the vertebral bodies, thereby enhancing the healing process.

BRIEF DESCRIPTION OF THE DRAWINGS

These and other features and advantages of the present invention will be better understood by reference to the following detailed description when considered in conjunction with the accompanying drawings wherein.

DETAILED DESCRIPTION OF THE PREFERRED EMBODIMENTS

An exemplary embodiment of the bone plate system according to the present invention is shown in FIGS. 1 to 5. The depicted bone plate system is particularly useful for stabilizing two or more vertebral bodies to allow fusion by holding the vertebral bodies in proper alignment, and thus allowing the bone to heal. The bone system of the invention is preferably weight-sharing over a period of at least about three months, and more preferably over a period of at least about six months. As used herein, the term "weight-sharing" as describing the system means that the system allows for partial sharing of the weight of one or more vertebral bodies across a bone graft site.

Generally, the bone plate system comprises a base plate 14, bone screws 16, and one or more interference devices 18. The base plate 14 is a plate used to connect two or more bones. As used herein, the term "bones" is intended to include both bones and bone fragments or portions. The base plate 14 can be of any suitable shape or size for the desired application.

Figure 2:
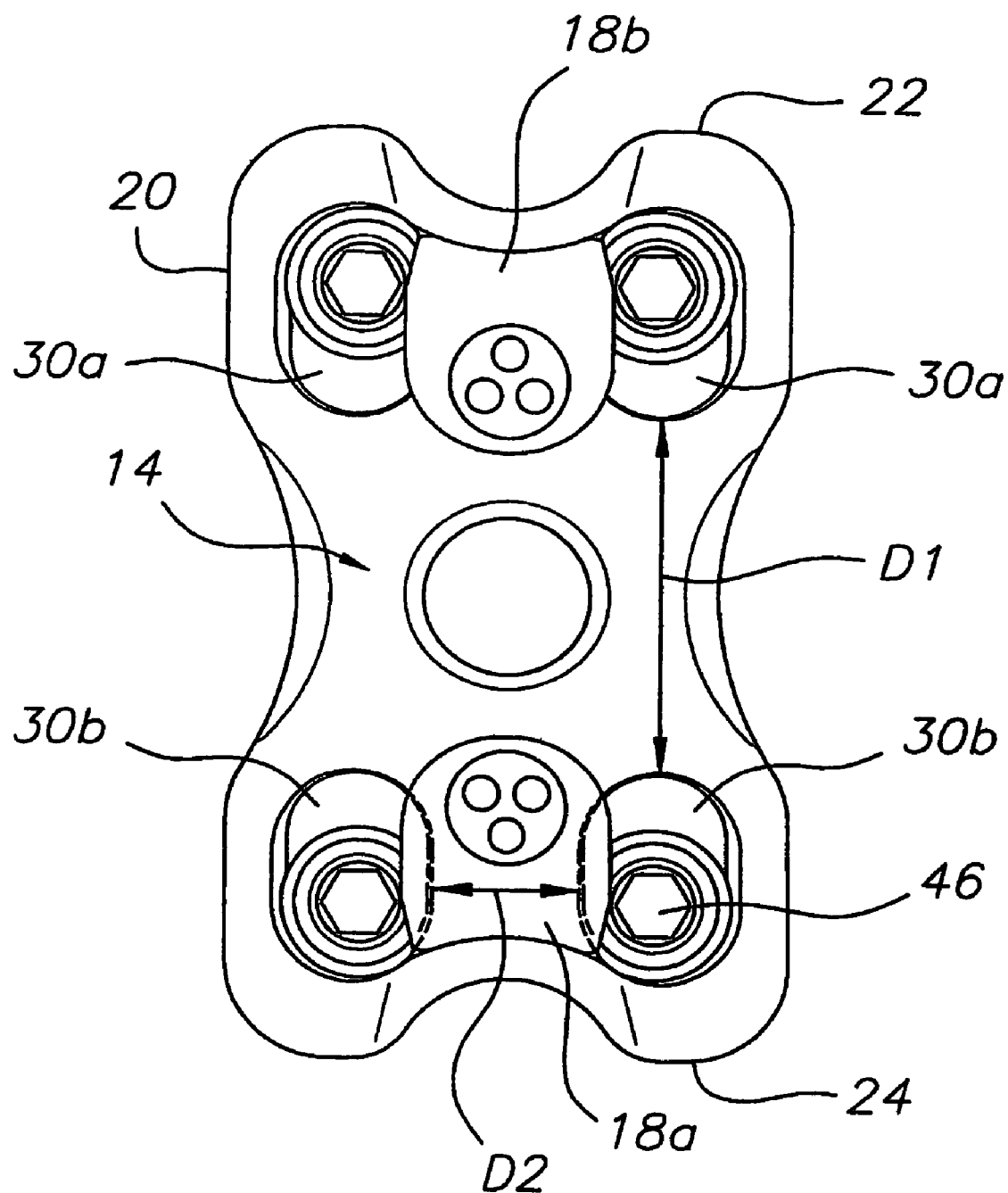
FIG. 2 is a top view of the bone plate system of FIG. 1.

In the depicted embodiment, the base plate 14 is a generally rectangular plate having two relatively long, generally parallel sides 20, a top end 22 and a bottom end 24, with the top end and bottom end also being generally parallel and shorter than the sides, as shown in FIG. 2. In the illustrated embodiment, each of the sides 20, top end 22 and bottom end 24 includes a region that is scalloped or concave. The concave regions are preferably located along the midsections of each of the sides 20, top end 22 and bottom end 24. As discussed further below, this scalloped or concave design is particularly desirable to prevent the base plate 14, when implanted, from interfering with the esophagus of the patient.

Figure 3:
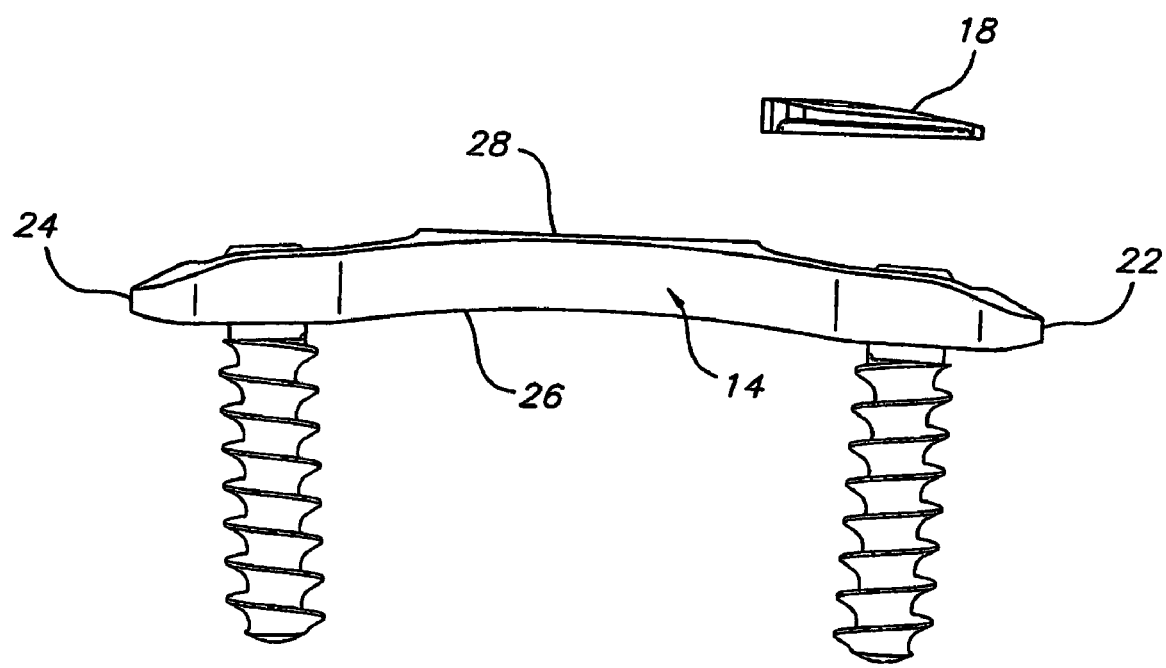
FIG. 3 is a side view of the bone plate system of FIG. 1.
Figure 4:
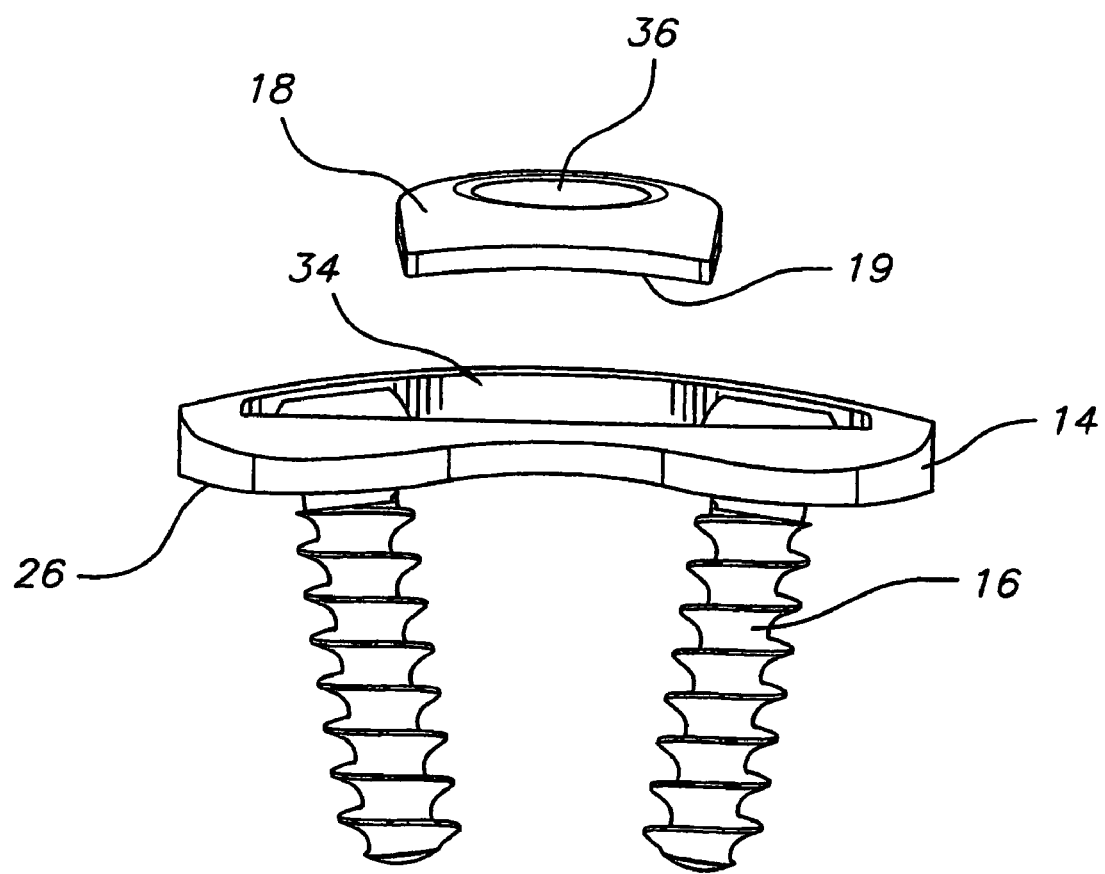
FIG. 4 is an end view of the bone plate system of FIG. 1.

When viewed from a side 20, the base plate 14 has a bottom surface that is slightly concave (along the length of the base plate), as best shown in FIG. 3. Similarly, when viewed from the top end 22 or the bottom end 24, the bottom surface of the base plate 14 is slightly concave (along the width of the base plate), as best shown in FIG. 4. This design permits the base plate 14 to be curved in the sagittal and horizontal planes to provide a better fit when implanted in a patient.

In one embodiment, the sides 20 each having a length ranging from about 20 mm to about 40 mm, and the top and bottom ends 22 and 24 each having a length ranging from about 14 mm to about 20 mm. The dimensions of the base plate 14 can vary depending upon the size of the patient in whom the plate is to be introduced. Further, the base plate 14 can have any other suitable shape, such as an oval shape.

The base plate 14 can be made of any suitable material, and is preferably made of titanium or a titanium alloy. If desired, the base plate 14 can also be part of a larger device.

The base plate 14 contains at least two bone screw slots 30 for receiving the bone screws 16. In the depicted embodiment, the base plate 14 contains four bone screw slots 30 arranged in two pairs. The bone screw slots 30*a* of the first pair are located nearer the top end 22 of the base plate 14, and the bone screw slots 30*b* of the second pair are located nearer the plate's bottom end 24. The bone screw slots 30*a* of the first pair are generally parallel to each other and to the sides 20 of the base plate 14. Similarly, the bone screw slots 30*b* of the second pair are generally parallel to each other and to the sides 20 of the base plate 14. The first pair of bone screw slots are 30*a* preferably generally aligned with the second pair of bone screw slots 30*b* and the pairs of slots positioned relative to the sides 20 and top and bottom ends 22 and 24 of the base plate 14 so as to create a generally symmetrical arrangement about the center of the base plate, as best shown in FIG. 2. The distance D1 between the pairs preferably ranges from about 6 mm to about 14 mm. The distance D2 between the slots 30*a* of the first pair preferably ranges from about 4 mm to about 8 mm.

In the depicted embodiment, all of the slots 30 have the same dimensions. The length of each slot preferably ranges from about 4 mm to about 8 mm, more preferably from about 6 mm to about 7 mm, still more preferably about 6.6 mm. The width of each slot preferably range from about 3 mm to about 6 mm, more preferably from about 4 mm to about 5.5 mm, still more preferably about 4.8 mm.

The depicted base plate 14 is particularly designed for the portion of the plate nearer the top end 22 to be attached to one vertebral body and the portion of the plate nearer the bottom end 24 to be attached to another vertebral body so that the plate is mounted in a vertical arrangement. The plate 14 has a bottom surface 26 that, in use, is adjacent to one or more of the bone surfaces, and a top surface 28 that faces away from the bone surface(s).

In the depicted embodiment, the bottom and top surfaces 26 and 28 are generally parallel to one another over a center region of the base plate 14, which encompasses the slots 30, so that in the center region the base plate has a generally uniform thickness, although the plate need not have a uniform thickness in this region. The top and bottom ends 22 and 24 of the base plate 14 are generally tapered, being thicker closer to the slots 30 and thinner closer to the edge of the plate 14, so that the bottom and top surfaces 26 and 28 are not parallel to one another at the top and bottom ends. Preferably the center region of the base plate 14, which encompasses the slots 30, has a thickness ranging from about 1 mm to about 4 mm, more preferably from about 2 mm to about 3 mm, still more preferably about 2.8 mm. The tapered top and bottom ends 22 and 24 each preferably taper to an edge thickness ranging from about 0.5 mm to about 2 mm, more preferably from about 0.5 mm to about 1.5 mm, still more preferably about 1 mm. The top and bottom ends 22 and 24 preferably taper at an angle ranging from about 20° to about 40°. This tapered end design is particularly beneficial in vertebral applications where the base plate 14 comes into contact with the esophagus. With the inventive tapered design, the esophagus is not positioned over a sharp corner, as in many plate designs, but instead is provided with a smooth transition surface as it passes over the inventive base plate, minimizing damage to the esophagus. In an alternative embodiment, only the top end 22 is provided with the tapered design, as the top end has the leading edge over which the esophagus interfaces. The tapered design in combination with the scalloped or concave design, discussed above, further enhances the ability of the plate system to avoid causing dysphagia.

The bone plate system of the invention includes a number of bones screws 16 that correspond to the number of bone screw slots 30, which in the depicted embodiment is four. In use, the bone screws 16 extend through the bone screw slots 30 in the base plate 14 and are screwed in to the bone. The bone screws 16 can be made of any suitable material, and are preferably made of the same material as the base plate, such as titanium or a titanium alloy. The shape and function of the bone screws are described in more detail below.

One or more interference devices 18 are provided to retain the bone screws 16 that extend through the bone screw slots 30 in the base plate 14. By "retain" is meant that an interference device 18 covers a sufficient portion of a bone screw 16 to prevent that bone screw from "backing out" out of the bone and base plate 14. The terminology "retain" is not intended to require that the entire top surface, or even the majority of the top surface, of a bone screw 16 be covered.

Figure 1:
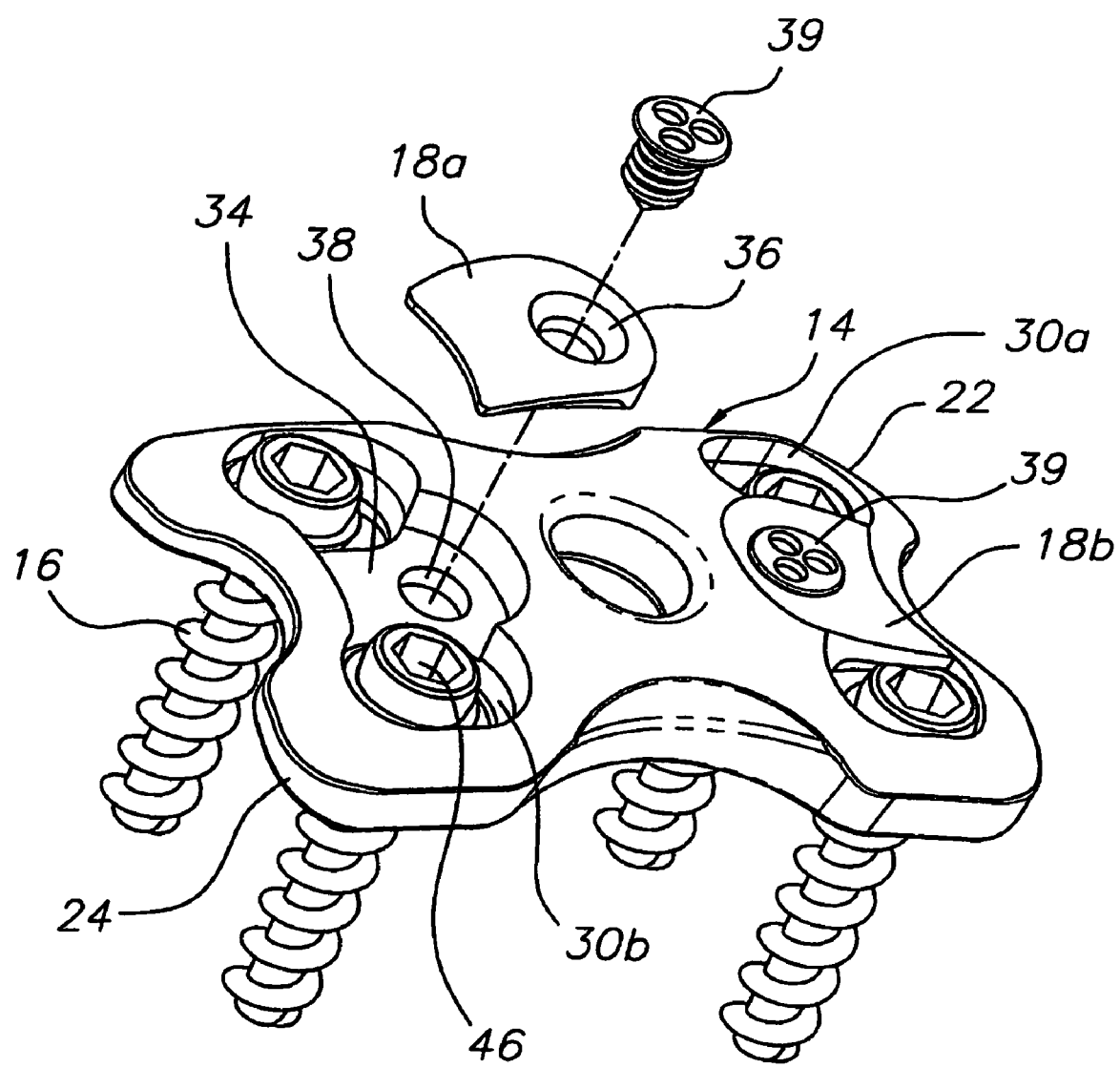
FIG. 1 is a perspective view of a bone plate system according to the present invention.

In the depicted embodiment, the bone plate system includes two interference device 18, each one for retaining a corresponding one of the two pairs of bone screws 16, so that one interference device 18*a* is provided nearer the bottom end 24 of the base plate 14 and the other interference device 18*b* is provided nearer the top end 22 of the base plate, as best shown in FIG. 1. Each interference device 18 is generally rectangular having a rounded top edge.

The thickness of each interference device 18 preferably ranges from about 0.5 mm to about 2 mm, and more preferably from about 1 mm to about 1.5 mm. As shown best in FIGS. 1 and 3, the edge of each interference device 18 that is positioned nearest the corresponding top or bottom end 22 or 24 of the base plate 14 is tapered in a manner similar to the top and bottom ends of the base plate.

In use, the interference devices 18 are removably fixedly attached to the base plate 14. As used herein, the term "fixedly attached" refers to the arrangement where the interference device 18, while being removably attached to the base plate 14, cannot slide relative to the base plate. The base plate 14 is preferably provided with recesses 34 to receive the interference device 18 and retain them in the desired position. The interference devices 18 can be removably attached to the base plate 14 by any suitable mechanism. In the depicted embodiment, each interference device 18 is provided with a cover screw hole 36.

The base plate 14 is provided with two cover screw aperture 38 that generally correspond in size and location to the cover screw holes 36 in the interference devices 18 when the interference devices are correctly positioned over the base plate. In the depicted embodiment, the cover screw apertures 38 are offset from the bone screw slots 30 in the base plate 14, as best shown in FIG. 1. By "offset" it is meant that the cover screw aperture 38 is provided at a position that does not fall on a line that passes through the centers of the bone screw slots 30, but instead that is offset from such a line, preferably in a direction closer to the center of the base plate 14.

To removably attach an interference device 18 to a base plate 14, a cover screw 39 is screwed into the cover screw hole 36 in the interference device and a corresponding cover screw aperture 38 in the base plate, as is generally known in the art. However, other mechanisms for attaching a interference device to a base plate known to those skilled in the art could also be used in accordance with the invention. If a different mechanism for attaching an interference device 18 is used, the point of attachment to the base plate 14 is preferably offset from the bone screw slots 30.

Figure 5:
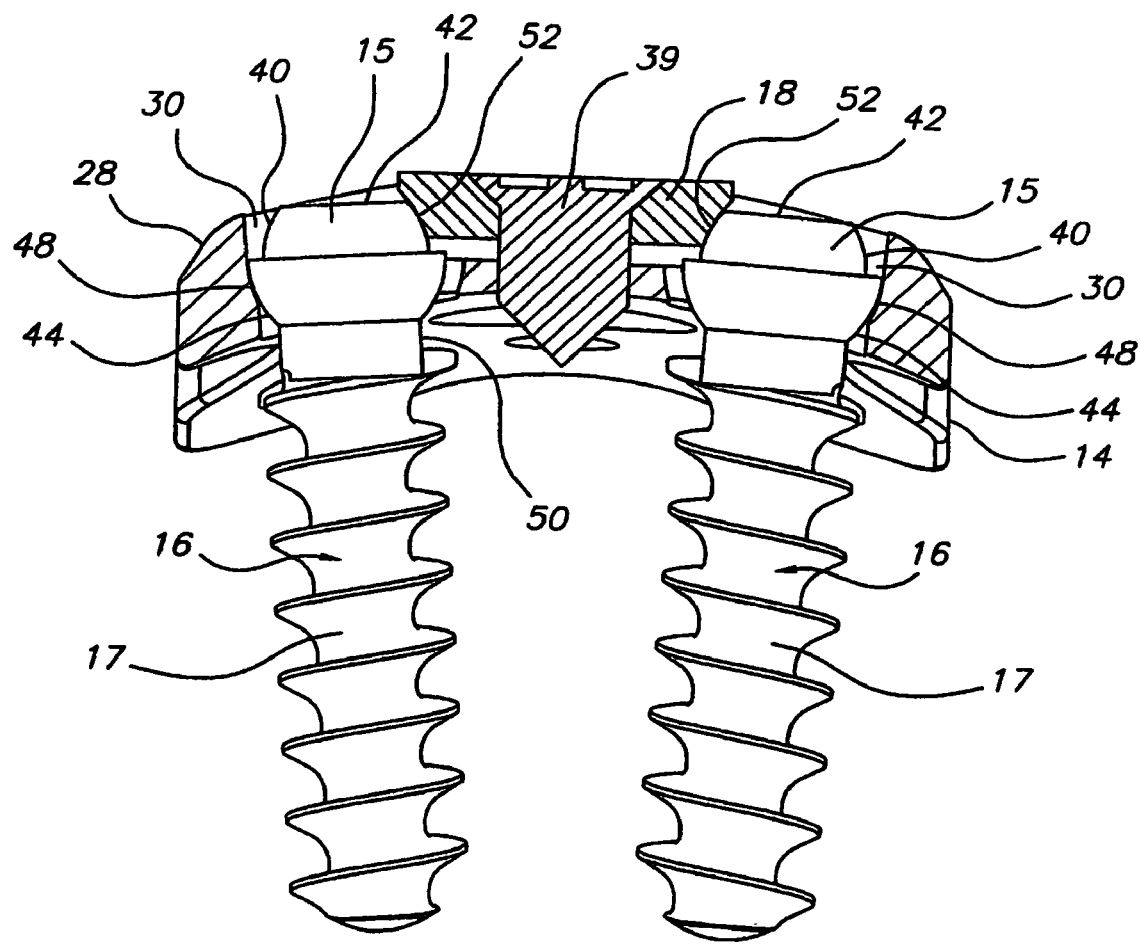
FIG. 5 is an end cross-sectional view of the bone screws inserted through the bone plate and covered by the interference device of a bone plate system as depicted in FIGS. 1 to 4.

FIG. 5 shows how the bone screws 16 are positioned relative to a base plate 14 and interference device 18. Each bone screw 16 comprises a screw head 15 and a threaded portion 17 extending from the screw head. Each bone screw head 15 has a generally rounded top surface 40, optionally with a generally flat center region 42, and a generally rounded bottom surface 44. The center region 42 of the generally rounded top surface 40 includes a hexagonal or other shaped aperture 46, as shown in FIGS. 1 and 2, for receiving the end of an insertion tool, as is generally known in the art.

Within the base plate 14, each bone screw slot 30 has a generally rounded edge surface 48 that interfaces with the bottom surface 44 of a corresponding bone screw head 15. An elongated axial opening 50 is provided along the bottom of each bone screw slot 30 to receive the threaded portion 17 of the bone screw 16 as the bone screw slides in the slot. The rounded edge surface 48 of the bone screw slot 30 joins the top surface 28 of the bone plate 14 to a top edge of the axial opening 50. The axial opening 50 has a width less than the width of the top portion of the bone screw slot 30, i.e., the portion of the bone screw slot receiving the screw head 15.

The interference device 18 has two generally rounded edge surfaces 52 that interfaces with the edges of the generally rounded top surfaces 40 of the bone screw heads 15 while not substantially covering the center region 42 of the bone screw head, to thereby prevent the bone screw 16 from backing out of the base plate 14. This design permits each bone screw 16 to toggle within its corresponding bone screw slot 30 while the interference device 18 still exerts sufficient force on the bone screw to control the degree to which the bone screw slides within the bone screw slot 30.

In the depicted embodiment, the rounded top surface 40 of each bone screw 16 has a maximum outer diameter less than the maximum outer diameter of the screw's rounded bottom surface 44. With this design, the rounded bottom surface 44 can be made sufficiently large to prevent the head of the bone screw 16 from passing through bone screw slot 30, while the rounded top surface 40 is smaller to permit the interference device 18 to still lower on the base plate 14, thus further reducing interference between the plate system and the esophagus.

In one embodiment, the interface of the top surface 40 of the bone screw head 15 and the edge surface 52 of the interference device 18 is provided to require a minimum force to cause the bone screw 16 to slide within the bone screw slot 30, thus permitting the bone screws to controllably slide in the bone screw slots. The minimum force preferably ranges from about 15 to about 50 pounds, more preferably from about 30 to 40 pounds. The system can be advantageously arranged to permit the bone screw 16 to both settle in a direct vertical plane of 1.5 mm to 2 mm and pivot under the interference device 18.

The offset location of the anchor or attachment point (i.e., the cover screw) of the interference device 18 to the base plate 14 advantageously provides increased resistance to screw sliding and toggling as vertebral bodies joined by the plate begin to settle. Specifically, when the bone screws 16 are first introduced into vertebral bodies through the base plate 14, they are introduced into the bone screw slots 30 closer to the top and bottom ends of the base plate (i.e., farther from the center of the base plate). In this location, the bone screws are permitted to toggle and slide fairly easily, which is desirable because it is advantageous to permit the plate system to initially engage the vertebral bodies and permit the vertebral bodies to settle on the graft fairly quickly. After initial settling has occurred, the base plate 14 moves relative to the bone screw 16, thereby positioning the bone screws closer to the center of the base plate. As the bone screws move toward the center of the base plate 14, they also mover nearer the cover screw or other point of attachment between the interference device and the base plate. At this point of attachment, the interference device exerts the greatest force on the bone screws 16. Thus, as the bone screws 16 move toward the point of attachment, the incremental force required to further move the bone screws toward the point of attachment (and thus toward the center of the plate) increases. Thus, the plate system advantageously controls further settling, thereby preventing the vertebral bodies from collapsing too quickly.

The preceding description has been presented with reference to presently preferred embodiments of the invention. Workers skilled in the art and technology to which this invention pertains will appreciate that alterations and changes in the described structures may be practiced without meaningfully departing from the principal, spirit and scope of this invention. Accordingly, the foregoing description should not be read as pertaining only to the precise structures described and illustrated in the accompanying drawings, but rather should be read consistent with and as support to the following claims which are to have their fullest and fair scope.

What is claimed is:

1. A method of performing surgery, comprising:
   inserting a bone plate having a first end and a second end and at least two generally parallel elongated screw slots therethrough;
   inserting a bone screw capable of securing the bone plate to a bone through each of said generally parallel elongated screw slots, said bone screw having a screw head and a threaded portion extending therefrom; and
   attaching an interference device to said bone plate, said interference device dimensioned to retain said bone plate, said interference device having an upper surface defining a first surface area and a lower surface defining a second surface area, wherein said first surface area is greater than said second surface area, wherein said lower surface includes at least one recess therein, and
   wherein said interference device is dimensioned to retain said bone screws while permitting the bone screws to toggle and controllably slide in said screw slots of said bone plate by a continuous engagement interface between the interference device and the bone screws, and
   wherein said interference device provides incrementally increasing resistance to sliding of the bone screws as the bone screws move away from said first end and said second end of the bone plate.

2. The method of claim 1, wherein said interference device is attached to said bone plate with cover screw that extends through a cover screw hole in the interference device and into a cover screw hole in said bone plate.

3. The method of claim 1, wherein said interference device is attached to the bone plate at a location that is offset from the bone screw slots.

4. A method for fusing a first bone segment and a second bone segment, said method comprising:
inserting a bone plate having first end and a second end and at least a first pair of screw slots located near said first end and a second pair of screw slots located near said second end;
positioning said bone plate such that said first end is associated with said first bone segment and said second end is associated with said second bone segment;
inserting a bone screw capable of securing said bone plate to a bone through each of said first and second pair of screw slots such that said first end is secured to said first bone segment and said second bone segment, said bone screw having head and threaded portion extending therefrom; and
attaching a first interference device dimensioned to retain said bone screws associated with said first pair of screw slots while permitting the bone screws to toggle and to controllably slide in the said first pair of screw slots by a continuous engagement interface between the first interference device and the bone screws, wherein said first interference device has an upper surface defining a first surface area and a lower surface defining a second surface area, wherein said first surface area is greater than said second surface area, and wherein said lower surface includes at least one recess, and
wherein said interference device provides incrementally increasing resistance to sliding of the bone screws as the bone screws move away from said first end and said second end of the bone plate.

5. The method of claim 4, further comprising:
attaching a second interference device to said bone plate, said second interference device dimensioned to retain said bone screws associated with said second pair of screw slots while permitting the bone screws to toggle and to controllably slide in said second pair of screw slots by continuous engagement interface between the second interference device and the bone screws.

6. The method of claim 4, wherein the bone plate has a center region of generally uniform thickness between said first and second ends, the center region encompassing a portion of first pair screw slots and a portion of the second pair of screw slots.

7. The method of claim 6, wherein said first end is generally tapered so that it is thicker closer to said first pair of screw slots and thinner closer to the edge of said bone plate.

* * * * *